United States Patent
Markle et al.

(10) Patent No.: US 6,790,683 B1
(45) Date of Patent: Sep. 14, 2004

(54) METHODS OF CONTROLLING WET CHEMICAL PROCESSES IN FORMING METAL SILICIDE REGIONS, AND SYSTEM FOR PERFORMING SAME

(75) Inventors: Richard J. Markle, Austin, TX (US); Terri A. Couteau, Rosanky, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 0 days.

(21) Appl. No.: 10/303,224

(22) Filed: Nov. 25, 2002

(51) Int. Cl.[7] .............................................. H01L 21/00
(52) U.S. Cl. .......................... 438/8; 438/747; 438/754; 438/16; 216/85
(58) Field of Search ............................... 438/8, 16, 747, 438/754, 85, 655, 664, 683; 216/84, 85

(56) References Cited

U.S. PATENT DOCUMENTS 4,208,240 A * 6/1980 Latos .......................... 216/60
6,458,711 B1 * 10/2002 O'Brien et al. ............. 438/745

* cited by examiner

Primary Examiner—George Fourson
Assistant Examiner—Julio J. Maldonado
(74) Attorney, Agent, or Firm—Williams, Morgan & Amerson, P.C.

(57) ABSTRACT

The present invention is generally directed to various methods of controlling wet chemical processes in forming metal silicide regions, and a system for performing same. In one illustrative embodiment, the method comprises providing a substrate having a layer of unreacted refractory metal and at least one metal silicide region formed thereabove, performing a wet chemical process to remove at least a portion of the layer of unreacted refractory metal, measuring at least one characteristic of the portion of the layer of unreacted refractory metal while the wet chemical process is being performed, and controlling at least one parameter of the wet chemical process based upon the measured at least one characteristic of the portion of the layer of unreacted refractory metal. In another illustrative embodiment, the method comprises providing a substrate having a layer of unreacted refractory metal and at least one metal silicide region formed thereabove, performing a wet chemical process to remove at least a portion of the layer of unreacted refractory metal, measuring at least one characteristic of the portion of the layer of unreacted refractory metal after at least some of the wet chemical process has been performed, and controlling at least one parameter of the wet chemical process based upon the measured at least one characteristic of the portion of the layer of unreacted refractory metal.

47 Claims, 6 Drawing Sheets

METHODS OF CONTROLLING WET CHEMICAL PROCESSES IN FORMING METAL SILICIDE REGIONS, AND SYSTEM FOR PERFORMING SAME

BACKGROUND OF THE INVENTION

1. Field of the Invention

This invention relates generally to semiconductor fabrication technology, and, more particularly, to various methods of controlling wet chemical processes in forming metal silicide regions, and a system for performing same.

2. Description of the Related Art

There is a constant drive within the semiconductor industry to increase the operating performance of integrated circuit devices, e.g., microprocessors, memory devices, and the like. This drive is fueled by consumer demands for computers and electronic devices that operate at increasingly greater speeds. This demand for increased speed has resulted in a continual reduction in the size of semiconductor devices, e.g., transistors. That is, many components of a typical field effect transistor (FET), e.g., channel length, junction depths, gate insulation thickness, and the like, are reduced. For example, all other things being equal, the smaller the channel length of the transistor, the faster the transistor will operate. Thus, there is a constant drive to reduce the size, or scale, of the components of a typical transistor to increase the overall speed of the transistor, as well as integrated circuit devices incorporating such transistors. Moreover, the density of such transistors on a wafer per unit area has dramatically increased as a result of, among other things, the reduction in feature sizes, and an overall desire to minimize the size of various integrated circuit products.

Figure 1:
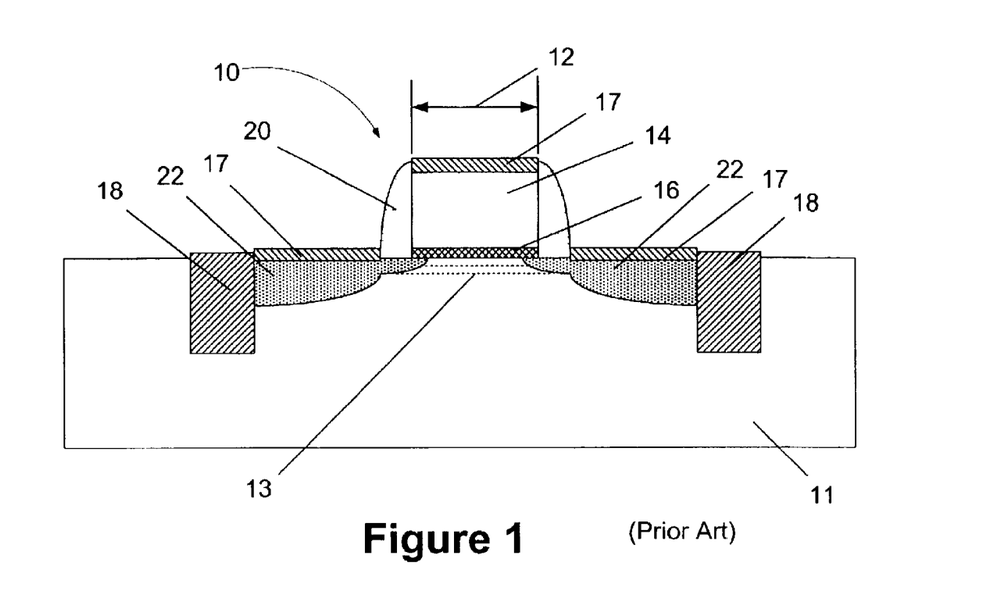
FIG. 1 is a cross-sectional view of an illustrative prior art transistor.

By way of background, modem integrated circuit devices, e.g., microprocessors, ASICs, memory devices, etc., are comprised of millions of field effect transistors formed on a semiconducting substrate, such as silicon. The substrate may be doped with either N-type or P-type dopant materials. An illustrative field effect transistor 10, as shown in FIG. 1, may have a doped polycrystalline silicon (polysilicon) gate electrode 14 formed above a gate insulation layer 16. The gate electrode 14 and the gate insulation layer 16 may be separated from doped source/drain regions 22 of the transistor 10 by a dielectric sidewall spacer 20. The source/drain regions 22 for the transistor 10 may be formed by performing one or more ion implantation processes to introduce dopant atoms, e.g., arsenic or phosphorous for NMOS devices, boron for PMOS devices, into the substrate 11. Shallow trench isolation regions 18 may be provided to isolate the transistor 10 electrically from neighboring semiconductor devices, such as other transistors (not shown). Additionally, although not depicted in FIG. 1, a typical integrated circuit product is comprised of a plurality of conductive interconnections, such as conductive lines and conductive contacts or vias, positioned in multiple layers of insulating material formed above the substrate. These conductive interconnections allow electrical signals to propagate between the transistors formed above the substrate.

The gate electrode 14 has a critical dimension 12, i.e., gate length, that approximately corresponds to the channel length 13 of the device when the transistor 10 is operational. Thus, it is very important that the critical dimension 12 of the gate electrode 14 be formed very accurately. Even small errors in the critical dimension 12 of the gate electrode 14 can result in the failure of the finished product to meet certain target electrical performance characteristics, e.g., switching speed, leakage current, etc. Of course, the critical dimension 12 of the gate electrode 14 is but one example of a feature that must be formed very accurately in modern semiconductor manufacturing operations. Other examples include, but are not limited to, conductive lines, openings in insulating layers to allow subsequent formation of a conductive interconnection, i.e., a conductive line or contact, therein, etc.

Also depicted in FIG. 1 are a plurality of metal silicide regions 17 that are formed above the gate electrode 14 and the source/drain regions 22. In general, one purpose of the metal silicide regions 17 is to reduce contact resistance and thereby enhance various operating characteristics of the transistor 10 and integrated circuit products, e.g., microprocessors, incorporating such transistors 10. The metal silicide regions 17 may be comprised of a variety of different materials, e.g., cobalt silicide, titanium silicide, nickel silicide, platinum silicide, tantalum silicide, tungsten silicide, etc.

Figure 2A:
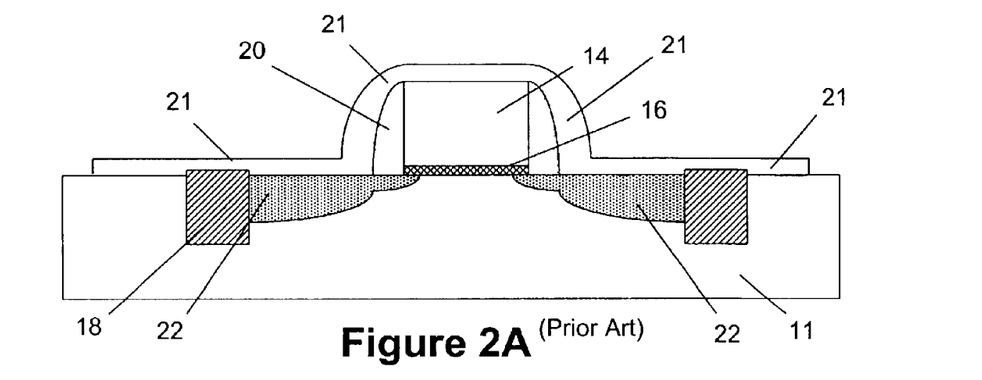
FIGS. 2A–2C are cross-sectional views of an illustrative transistor wherein metal silicide regions are formed above the transistor in accordance with one illustrative prior art process flow.
Figure 2B:
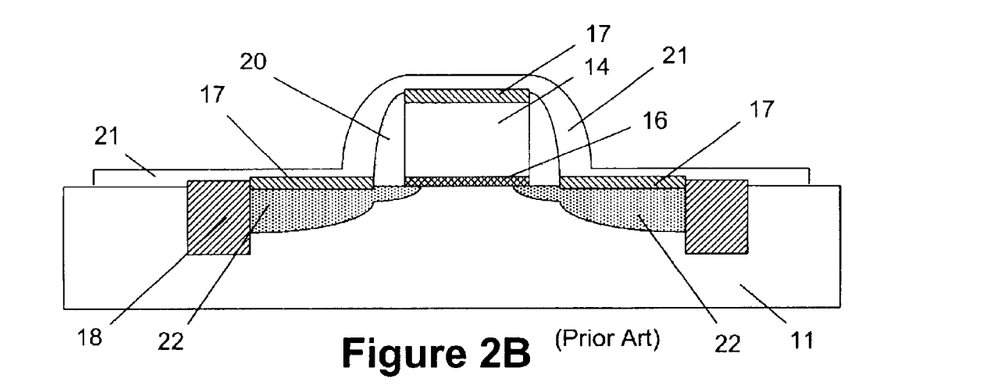
Figure 2C:
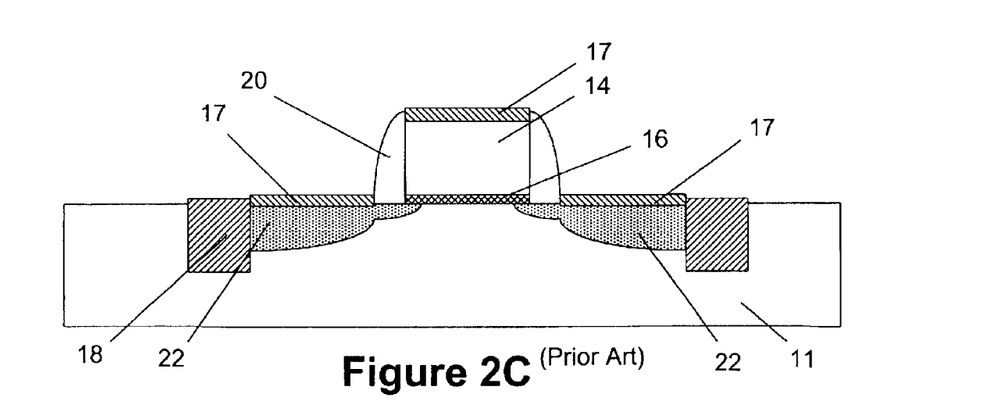

The metal silicide regions 17 may be formed by a variety of known techniques. One illustrative process flow for forming the metal silicide regions 17 is depicted in FIGS. 2A–2C. Initially, as shown in FIG. 2A, a layer of refractory metal 21 is deposited above the gate electrode 14 and the source/drain regions 22. Thereafter, one or more anneal processes are performed to convert portions of the layer of refractory metal 21 in contact with the silicon-containing gate electrode 14 and source/drain regions 22 into the metal silicide regions 17, as indicated in FIG. 2B. Then, a wet chemical process is performed to remove unreacted portions of the layer of refractory metal 21, as shown in FIG. 2C.

Referring back to FIG. 1, using current-day technology, the channel length 13 of modem transistors may be approximately 120–180 nm, and further reductions are planned in the future. The reduction in the channel length 13 of the transistor 10 also requires a reduction in the physical size of other components of the transistor 10. For example, the depth of the source/drain regions 22 is also reduced along with the length 12 of the gate electrode 14. As a result of the dramatic reduction of device dimensions, other aspects of the transistor 10 may act to limit the performance characteristics of the transistor. Stated another way, the performance of the transistor 10 may not be limited solely by the channel length 13 of the transistor 10, but rather by the RC-time delay associated with the propagation of electrical signals in an integrated circuit device and within the transistor 10. For example, delays associated with the propagation of an electrical signal along the width, i.e., into the drawing page, of the gate electrode 14 (to turn the transistor "ON") may act to limit one or more operating characteristics of the transistor 10. Similarly, signal propagation may be limited through the source/drain regions 22 of the transistor 10. However, the thickness of metal silicide regions 17 on the source/drain regions 22 must be limited so as not to consume too much of the underlying source/drain regions 22 during the formation process.

In some cases, the process parameters used in forming metal silicide regions 17, e.g., anneal temperatures and duration, the duration of wet chemical processes, etc., may be determined by performing various tests on a number of test wafers. In other cases, e.g., removal of unreacted refractory metal 21, a wet chemical process is performed for a duration that is assumed to be sufficient for the maximum anticipated thickness of the originally formed layer of refractory metal 21. However, the duration of the wet chemical process determined using this "worst case" type approach may unduly consume other components of the transistor 10 if the layer of refractory metal 21 is thinner than the anticipated "worst-case" thickness. For example, depending upon the composition of the material used for the sidewall spacers 20, if the wet chemical process is performed for too long of a duration, it may consume too much of the sidewall spacers 20. As another example, excessive time in the chemical bath may consume some of the metal silicide regions 17.

Additionally, the anneal processes performed to form the metal silicide regions 17 is typically a timed process that is performed for the specified duration set by the particular process flow. Similarly, the wet chemical process performed to remove the unreacted refractory metal is also a timed process. Such fixed, inflexible processing methodologies may inhibit the formation of metal silicide regions 17 exhibiting the desired characteristics. In some cases, such fixed, inflexible processing techniques may result in the production of integrated circuit products that do not exhibit the desired performance characteristics.

The present invention is directed to various methods and systems that may solve, or at least reduce, some or all of the aforementioned problems.

SUMMARY OF THE INVENTION

The present invention is generally directed to various methods of controlling wet chemical processes in forming metal silicide regions, and a system for performing same. In one illustrative embodiment, the method comprises providing a substrate having a layer of unreacted refractory metal and at least one metal silicide region formed thereabove, performing a wet chemical process to remove at least a portion of the layer of unreacted refractory metal, measuring at least one characteristic of the portion of the layer of unreacted refractory metal while the wet chemical process is being performed, and controlling at least one parameter of the wet chemical process based upon the measured characteristic of the portion of the layer of unreacted refractory metal.

In another illustrative embodiment, the method comprises providing a substrate having a layer of unreacted refractory metal and at least one metal silicide region formed thereabove, performing a wet chemical process to remove at least a portion of the layer of unreacted refractory metal, measuring at least one characteristic of the portion of the layer of unreacted refractory metal after at least some of the wet chemical process has been performed, and controlling at least one parameter of the wet chemical process based upon the measured characteristic of the portion of the layer of unreacted refractory metal.

In yet another illustrative embodiment, the method comprises providing a substrate having a layer of unreacted refractory metal and at least one metal silicide region formed thereabove, measuring at least one characteristic of at least a portion of the layer of unreacted refractory metal, determining at least one parameter of a wet chemical process to be performed to remove the layer of unreacted refractory metal based upon the measured characteristic, and performing the wet chemical process comprised of the determined parameter on the layer of unreacted refractory metal.

In a further illustrative embodiment, the method comprises providing a substrate having a layer of unreacted refractory metal and at least one metal silicide region formed thereabove, performing a wet chemical process to remove the layer of unreacted refractory metal, measuring at least a thickness of at least a portion of the layer of unreacted refractory metal after at least some of the wet chemical process has been performed, and controlling at least one parameter of the wet chemical process based upon the measured thickness of the portion of the layer of unreacted refractory metal.

In still a further illustrative embodiment, the method comprises providing a substrate having a layer of unreacted refractory metal and at least one metal silicide region formed thereabove, performing a wet chemical process to remove at least a portion of the layer of unreacted refractory metal, measuring a thickness of the metal silicide region at some point after the wet chemical process has been performed, and controlling at least one parameter of the wet chemical process based upon the measured thickness of the metal silicide region.

In yet a further illustrative embodiment, the method comprises providing a substrate having a layer of unreacted refractory metal and at least one metal silicide region formed thereabove, performing a wet chemical process to remove at least a portion of the layer of unreacted refractory metal, measuring a thickness of the metal silicide region at some point after the wet chemical process has been performed, and performing the wet chemical process for a fixed duration after the measured thickness has reached a preselected value.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers'specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various structures of the semiconductor device, the silicide regions and the layer of refractory metal are depicted in the drawings as having very precise, sharp configurations and profiles, those skilled in the art recognize that, in reality, these regions, structures and layers may not be as precise as indicated in the drawings. Additionally, the relative sizes of the various features and silicide regions depicted in the drawings may be exaggerated or reduced as compared to the size of those features or regions on fabricated devices. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In general, the present invention is directed to various methods of controlling wet chemical processes in forming metal silicide regions, and a system for performing same. As will be readily apparent to those skilled in the art upon a complete reading of the present application, the present invention may be employed in connection with the formation of metal silicide regions comprised of a variety of different metal silicides, e.g., cobalt silicide, titanium silicide, tantalum silicide, nickel silicide, platinum silicide, tungsten silicide, etc. Moreover, the present invention may be employed in the context of forming metal silicide regions on any of a variety of different types of semiconductor devices, e.g., transistors, resistors, capacitors, memory cells, light emitting diodes, etc., and it may be employed in connection with the formation of a variety of different types of integrated circuit products, including, but not limited to, logic products, memory products, etc. For convenience, the present invention will be disclosed in the context of the formation of metal silicide regions above an illustrative transistor. However, the present invention should not be considered as limited to the formation of any particular type of metal silicide or to the formation of the metal silicide regions on any particular type of semiconductor device or product unless such limitations are clearly set forth in the appended claims.

The present invention is generally related to a previously filed application, Ser. No. 09/863,596, entitled "Method and Apparatus for Determining Process Layer Thickness Using Scatterometry Measurements," filed May 23, 2001. That application is currently assigned to the assignee of the present invention, Advanced Micro Devices, Inc. The present invention is also related to application Ser. No. 10/304,114, entitled "Methods of Controlling Formation of Metal Silicide Regions, and System for Performing Same," filed concurrently with the present application, both of which are hereby incorporated by reference in their entirety.

In general, the formation of metal silicide regions involves depositing a layer of refractory metal on a silicon-containing structure or feature, performing one or more anneal processes to convert at least a portion of the layer of refractory metal into a metal silicide in regions where the refractory metal layer is in contact with the silicon-containing feature, and performing a wet chemical process to remove unreacted portions of the layer of refractory metal. In some cases, a two-step anneal process may be performed to form the metal silicide regions. Moreover, in some other situations, a first anneal process may be performed to initially form a less stable form of metal silicide, followed by a wet chemical process to remove the unreacted refractory metal. Then, a second anneal process may be performed to form a more stable type of metal silicide. The present invention may also be employed in cases where different types of metal silicides that may have differing thicknesses are formed above a semiconductor device. For example, a relatively thick layer of titanium silicide may be formed above the gate electrode 14 while a relatively thin layer of cobalt silicide may be formed above the source/drain regions 22. However, as will be recognized by those skilled in the art after a complete reading of the present application, the present invention is not limited to any particular process flow used to form such metal silicide regions or to any specific material for the metal silicide regions. Thus, such details should not be considered a limitation of the present invention unless such limitations are clearly set forth in the appended claims.

The layer of refractory metal 21 (see FIGS. 4A–4B) may be formed by, for example, a physical vapor deposition (PVD) process or a chemical vapor deposition (CVD) process, and it may be comprised of a variety of materials, e.g., cobalt, nickel, titanium, tantalum, platinum, tungsten, etc. Moreover, the thickness of the layer of refractory metal 21 may vary depending upon the particular application. For example, the layer of refractory metal may vary from approximately 50–300 nm. Thus, the particular type of refractory metal employed, and the manner in which it is made should not be considered a limitation of the present invention.

In one embodiment, a grating structure is formed that is comprised of a plurality of features upon which metal silicide regions will be formed. The particular feature may vary depending upon the application. For example, the features may be a plurality of line-type features, such as gate electrode structures, or a plurality of doped regions in a substrate, such as source/drain regions. The features may be part of actual production devices or they may be separate test structures formed on a substrate. The physical size of the grating structures, as well as the number of features that comprise each grating structure, may vary depending upon the application.

Figure 3A:
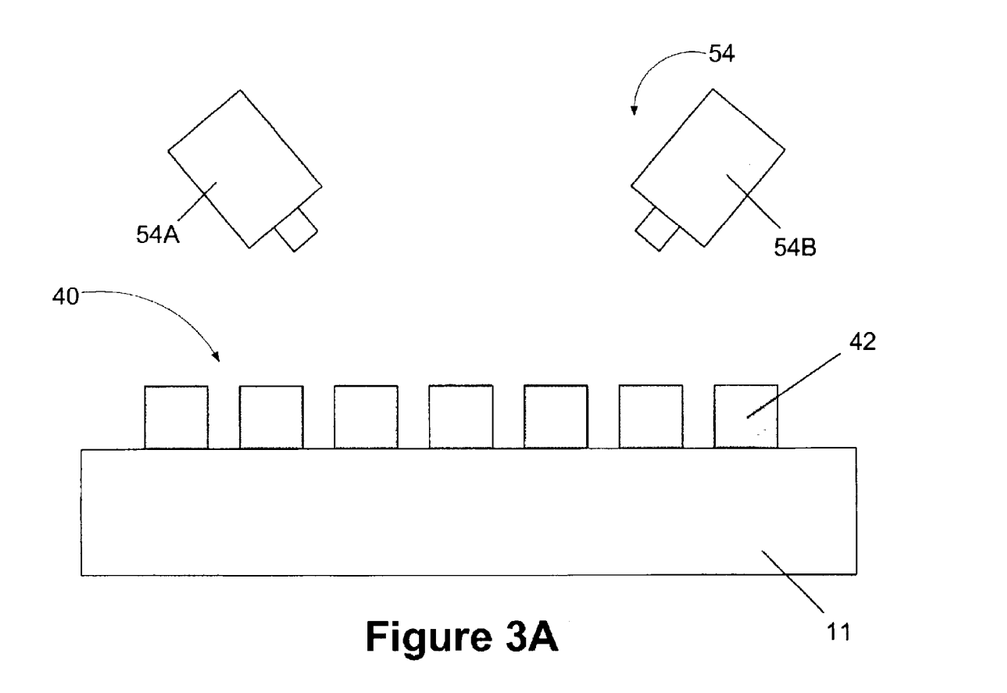
FIG. 3A depicts an illustrative grating structure comprised of a plurality of features.

An illustrative grating structure 40 is schematically depicted in FIG. 3A. As described more fully herein, metal silicide regions may be formed on one or more of the features 42 of the grating structure 40. Thereafter, a wet chemical process may be performed to remove or strip the unreacted portions of the layer of refractory metal 21. In various aspects of the present invention, optical measurements, such as scatterometric measurements, of the layer of unreacted refractory metal 21 and/or the metal silicide regions 17 may be performed to control one or more aspects of the wet chemical process. As schematically depicted in FIG. 3A, such scatterometric measurements may be made using a scatterometry tool 54 that is comprised of an illustrative light source 54A and a detector 54B. As stated previously, the features 42 may be any type of structure, e.g., gate electrodes, doped regions, memory cells, etc. For ease of discussion, the features 42 are simply depicted as line-type features.

Figure 3B:
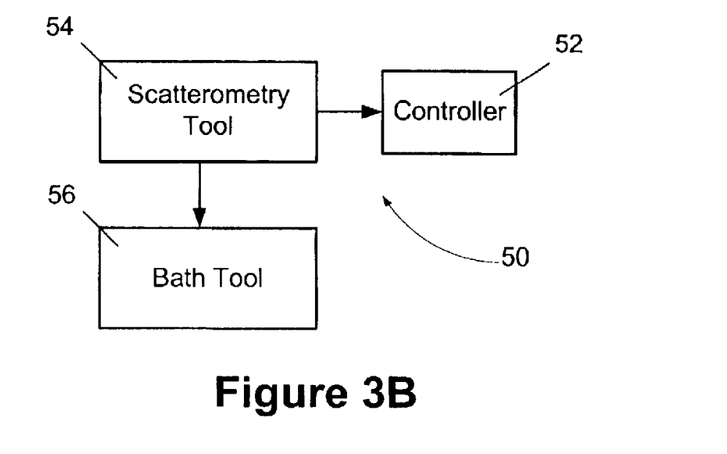
FIG. 3B depicts a system in accordance with one illustrative embodiment of the present invention.
Figure 3C:
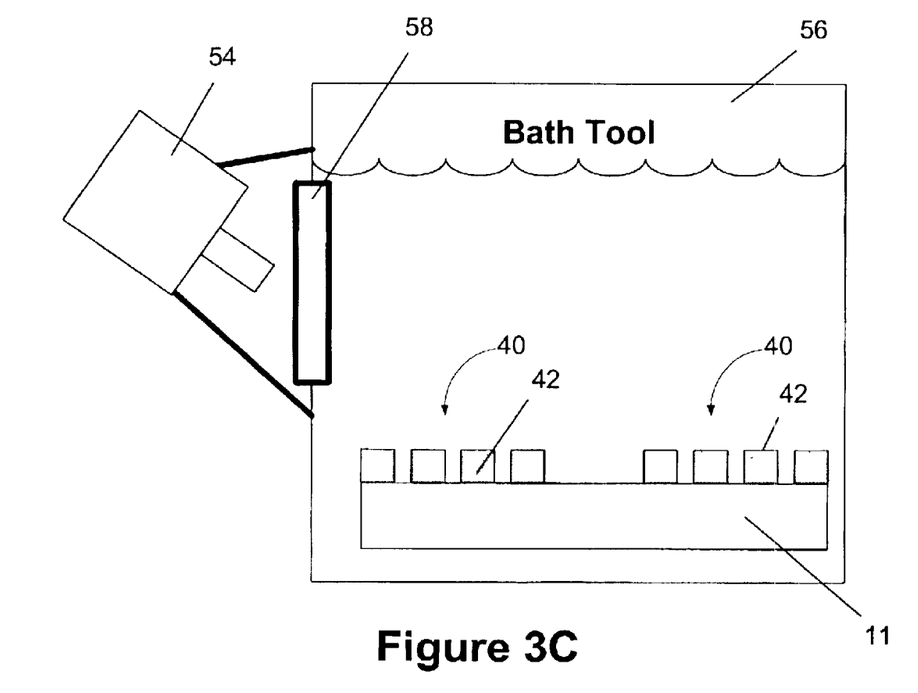
FIG. 3C depicts an illustrative chemical bath tool in accordance with one illustrative embodiment of the present invention.
Figure 3D:
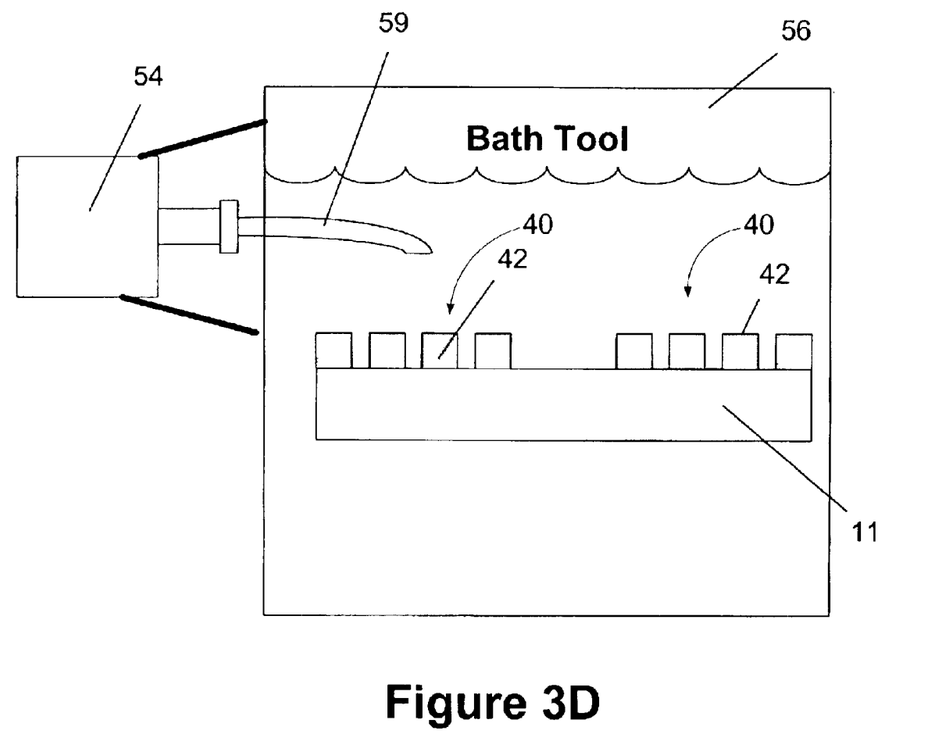
FIG. 3D depicts an illustrative chemical bath tool in accordance with yet another illustrative embodiment of the present invention.

FIG. 3B depicts an illustrative system 50 that may be used in accordance with one embodiment of the present invention. As shown therein, the system 50 is comprised of a controller 52, a scatterometry tool 54 and a chemical bath tool 56. In accordance with one aspect of the present invention, data obtained by the scatterometry tool 54 is used to control one or more parameters of the wet chemical process performed in the chemical bath tool 56 based upon scatterometric measurements of the unreacted layer of refractory metal 21 and/or the metal silicide regions 17. FIG. 3C depicts an illustrative embodiment of the chemical bath tool 56 wherein the scatterometry tool 54 is adapted to take scatterometric measurements of the unreacted refractory metal 21 and/or metal silicide region 17 through a window 58. In another embodiment depicted in FIG. 3D, an optical fiber 59 is positioned inside the liquid bath of the chemical bath tool 56 to thereby allow scatterometric measurements of the unreacted refractory metal 21 and/or the metal silicide regions 17. That is, in accordance with one aspect of the present invention, the scatterometry tool 54 may be used to take in situ measurements of the unreacted refractory metal 21 and/or the metal silicide regions 17 at some point after the wet chemical process has begun and, in some cases, as the wet chemical process is being performed in the chemical bath tool 56. In the illustrative example depicted in FIGS. 3C–3D, the wafer 11 is depicted as having two representative grating structures 40 formed above the wafer 11. However, as will be understood by those skilled in the art after a complete reading of the present application, the number of grating structures 40 formed above the wafer 11, as well as the number and type of features 42 that make up such grating structures, may vary, e.g., one or more grating structures may be employed.

As will be recognized by those skilled in the art after a complete reading of the present application, the present invention may be employed with any type of wet chemical process used to remove unreacted refractory metal in connection with the formation of metal silicide regions. Moreover, the present invention may be employed with any type of chemical bath tool 56 capable of performing the activities described herein. The present invention may be employed with any type of wet chemical process. For example, such a chemical process may be performed using a bath comprised of ammonium hydroxide, ammonium hydroxide and hydrogen peroxide, or sulfuric acid and hydrogen peroxide.

In one embodiment, the present invention may be employed to control or adjust one or more parameters of the wet chemical process performed in the chemical bath tool 56. More specifically, after the metal silicide regions 17 are formed, a characteristic of the unreacted refractory metal 21, such as thickness, surface profile (surface irregularities, agglomerations), chemical stoichiometry, etc., may be determined and fed forward to the chemical bath tool 56, via the controller 52, to control at least one parameter of the wet chemical process, e.g., duration, temperature, etchant concentration, etc., performed in the chemical bath tool 56. In one particular embodiment, the thickness measurement of the unreacted refractory metal may be measured using the scatterometry tool 54. The thickness of the unreacted refractory metal that is used in this aspect may be an average thickness or a thickness of a particular area of the refractory metal layer 21 that, through experience, is known to be the region of greatest thickness. By controlling the wet chemical process based upon the measured characteristic, e.g., thickness, of the unreacted refractory metal 21 to be removed, better control may be achieved and the chances of processing errors occurring are reduced. That is, rather than process all wafers based upon an assumed worst-case scenario, the wet chemical process may be tailored to reflect actual conditions. As a result, errors such as over-etching and under-etching may be reduced.

Figure 4A:
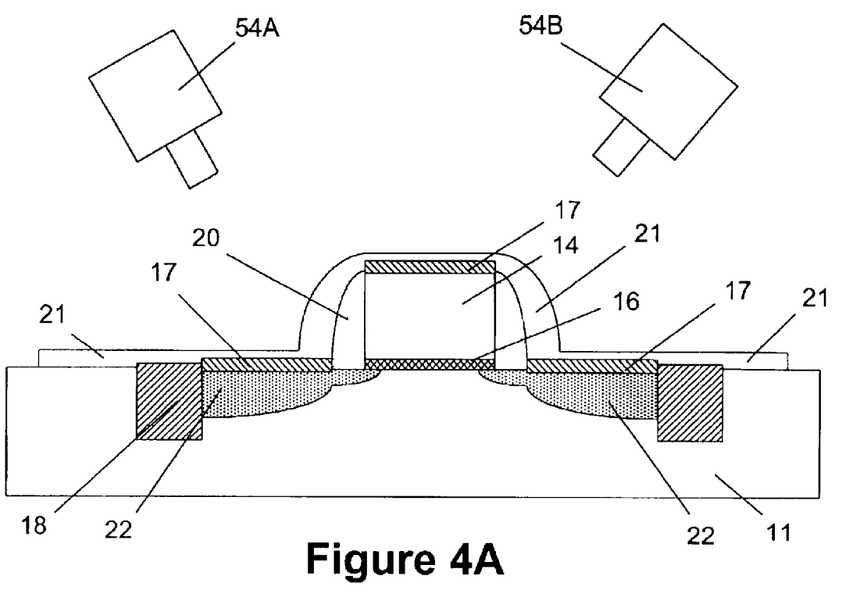
FIGS. 4A–4B depict an illustrative transistor having metal silicide regions and a layer of unreacted refractory metal formed thereabove wherein the removal of the unreacted refractory metal is controlled in accordance with one embodiment of the present invention.
Figure 4B:
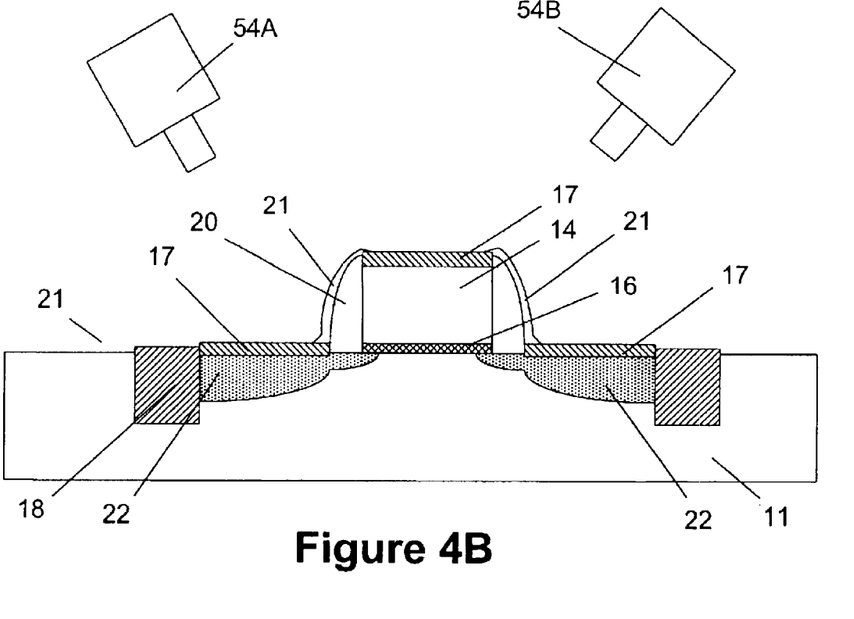

FIGS. 4A–4B depict another example where the present invention may be employed. In this example, the grating structures 40 are comprised of a plurality of transistors 10 wherein metal silicide regions 17 are formed on the gate electrode 14 and the source/drain regions 22. In general, in one aspect of the present invention, the wet chemical process may be endpointed based upon scatterometric measurements of the unreacted refractory metal 21 and/or metal silicide regions 17. FIG. 4A depicts the situation where the metal silicide regions 17 have been formed and the wafer 11 is initially placed in the chemical bath tool 56, e.g., the situation where the thickness of the unreacted refractory metal 21 is at a maximum. FIG. 4B depicts a point in the process where some of the refractory metal 21 has been removed while some still remains on the sidewall spacers 20. In this situation, the scatterometry tool 54, comprised of an illustrative light source 54A and detector 54B, is used to illuminate the unreacted refractory metal 21 at some point after the wet chemical process is started and to collect light reflected from the unreacted refractory metal 21. As the unreacted refractory metal is being removed or stripped, the optical characteristics, e.g., index of refraction ("n") and extinction coefficient ("k"), of the remaining unreacted refractory metal may change. Based upon these scatterometric measurements, various characteristics of the unreacted refractory metal may be determined, such as its thickness. When the thickness of the remaining unreacted refractory metal 21 is determined to be approximately zero, i.e., when all or virtually all of the unreacted refractory metal 21 has been cleared, the wet chemical process may be stopped. In another example, when the scatterometric measurements of the unreacted refractory metal 21 indicates that a very small amount of material remains, e.g., 1–2 nm, then the wet chemical process may be continued for a fixed amount of time that, based upon experience, is sufficient to clear the small remaining amount of the unreacted refractory metal 21. By limiting this timed wet chemical process to a time period necessary to clear the small amount of remaining unreacted refractory metal 21, the chances of causing damage due to over-etching is greatly limited.

Figure 5A:
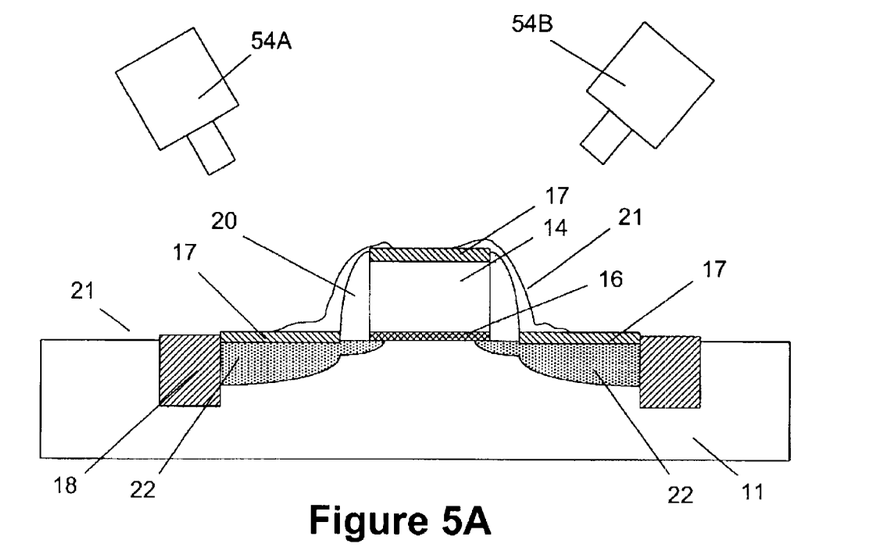
FIGS. 5A–5B depict another illustrative transistor having metal silicide regions and a layer of unreacted refractory metal formed thereabove wherein the removal of the unreacted refractory metal is controlled in accordance with another embodiment of the present invention.
Figure 5B:
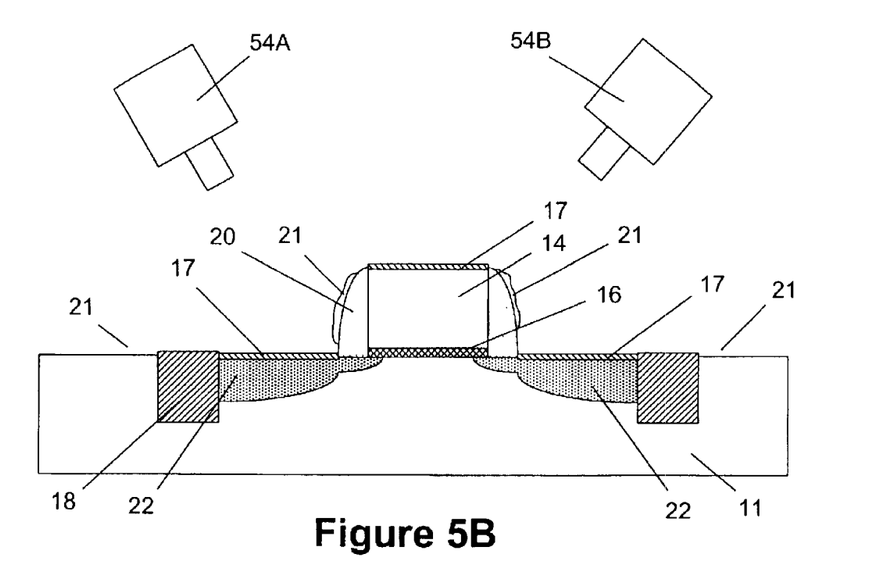

FIGS. 5A–5B depict another example of how the present invention may be employed. In general, the present invention may be used to control the wet chemical process based upon the thickness of the metal silicide regions 17. That is, irrespective of any other considerations, the wet chemical process may be stopped if the metrology data obtained by the scatterometry tool 54 indicates that the thickness of the metal silicide region 17 is at or near a minimum acceptable value. For example, FIG. 5A depicts the situation where the metal silicide regions 17 are at their maximum thickness having just been formed. FIG. 5B depicts the situation where some of the unreacted refractory metal 21 has been cleared, but the thickness of the metal silicide region 17 has reached a preselected minimum acceptable thickness. Thus, using this technique, a minimum thickness of the metal silicide regions 17 may be established, and, based upon scatterometric measurements of the metal silicide regions 17, this preselected minimum thickness may be used to, if necessary, stop the wet chemical process. Using this technique, undesirable consumption of the metal silicide regions 17, i.e., consumption beyond the allowed minimum thickness, may be prevented.

The metrology data from the scatterometry tool 54 may be provided to the controller 52. Based upon an analysis of the data obtained by the scatterometry tool 54, the controller 52 may control one or more parameters of the wet chemical process performed in the chemical bath tool 56. For example, the controller 52 may act to increase or decrease the concentration of one or more etchants in the liquid bath, increase or decrease the concentration of one or more etchants, increase or decrease the temperature of the chemical bath, change liquid recirculation flow rates, and/or stop (endpoint) the wet chemical process, etc. In one particularly illustrative embodiment, the controller 52 may be used to stop the wet chemical process when the data from the scatterometry tool 54 indicates that the unreacted refractory metal 21 has been cleared or when the metal silicide regions 17 have reached a minimum acceptable thickness.

In another illustrative embodiment, the data obtained by the scatterometry tool 54 may be used to control or adjust at least one parameter of a wet chemical process to be performed in removing unreacted refractory metal 21 on a subsequently processed substrate. That is, in this embodiment, the scatterometric data may be used to regulate the wet chemical process performed on subsequently processed substrates in the chemical bath tool 56.

A variety of scatterometry type tools may be used with the present invention, e.g., so-called 2θ-type systems and lens-type scatterometry tools. The scatterometry tool 54 may use white light, or light at some other wavelength or combination of wavelengths, depending on the specific implementation. Typically, the light source 54A will generate an incident beam that has a wide spectral composition and wherein the intensity of the reflected light changes slowly in comparison to changes in wavelength. The angle of incidence of the light may also vary, depending on the specific implementation. For example, a spectroscopic ellipsometer (single angle, many wavelengths), or a laser (single wavelength, many angles) may be used with the present invention. Additionally, the light source 54A and the detector 54B may be arranged in a concentric circle configuration, with the light source 54A illuminating the metal silicide regions from a perpendicular orientation, e.g., a reflectometer. The intensity of the reflected light may be measured as s- and p- polarization over either multiple angles or at multiple wavelengths.

In general, the scatterometry tool 54 includes optical hardware, such as an ellipsometer or reflectometer, and a data processing unit loaded with a scatterometry software application for processing data collected by the optical hardware. For example, the optical hardware may include a Model OP5230 or OP5240 with a spectroscopic ellipsometer offered by Thermawave, Inc. of Fremont, Calif. The data processing unit may comprise a profile application server manufactured by Timbre Technologies, Inc., a fully owned subsidiary of Tokyo Electron America, Inc. of Austin, Tex. and distributed by Thermawave, Inc.

In the illustrated embodiment, the controller 52 is a computer programmed with software to implement the functions described herein. Moreover, the functions described for the controller 52 may be performed by one or more controllers spread through the system. For example, the controller 52 may be a fab level controller that is used to control processing operations throughout all or a portion of a semiconductor manufacturing facility. Alternatively, the controller 52 may be a lower level computer that controls only portions or cells of the manufacturing facility. Moreover, the controller 52 may be a stand-alone device, or it may reside on the scatterometry tool 54 or the chemical bath tool 56. However, as will be appreciated by those of ordinary skill in the art, the controller 52 may comprise a hardware controller designed to implement the particular functions.

Variations in one or more of the characteristics of the unreacted refractory metal 21 and/or the metal silicide regions 17, e.g., thickness, surface profile, etc., will cause a change in the diffraction characteristics of the incident light from the light source 54A. In some aspects, the present invention involves measuring the thickness of the unreacted refractory metal 21. This may be accomplished by taking scatterometric measurements of the unreacted refractory metal 21 and comparing the scatterometric trace generated during the measurement process to a library of scatterometric traces, each of which correspond to a given thickness of unreacted refractory metal. Such a library of traces may be created by calculation, based upon Maxwell's equations, for a vast variety of anticipated thicknesses of the unreacted refractory metal. Thereafter, using known matching techniques, a scatterometric trace may be generated by the scatterometry tool 54 and this generated scatterometric trace may be matched to the closest corresponding trace in the library. Based upon this match, the measured unreacted refractory metal 21 is determined to have a characteristic, e.g., thickness, that corresponds to the characteristic associated with the matched trace from the library. Scatterometry libraries are commercially available from Timbre Technologies, Inc. Although not necessary, if desired, the library of calculated profile traces may be confirmed by various destructive metrology tests, where a scatterometry profile trace is generated and the actual characteristic, e.g., thickness, of the unreacted refractory metal 21 is subsequently measured using a scanning electron microscope metrology technique. Obviously, the number of combinations used to create the library may vary as a matter of design choice. Moreover, the greater the number of combinations, the greater will be the library containing the appropriate signature profiles of the implant regions.

In another aspect, the present invention may involve measuring a thickness of the metal silicide regions 17 at some time after the wet chemical process has been started. In some cases, such measurements may be made as the wet chemical process is being performed. Similar to the description above, a library of scatterometric traces may be created for metal silicide regions having a variety of anticipated thicknesses. Thereafter, the metal silicide regions 17 formed on the substrate may be measured using the scatterometry tool 54. The scatterometric trace produced during the scatterometric measurement process may then be matched to one of the traces in the library to determine the thickness of the measured metal silicide region 17.

Based upon this determined thickness of the metal silicide regions 17, various control actions may be taken with respect to the wet chemical process. For example, based upon this determined thickness of the metal silicide region 17, it may be confirmed that the wet chemical process can continue in its most aggressive manner. In other situations, it may be determined that the thickness of the metal silicide region 17 is approaching a minimum acceptable thickness. In such a situation, the etchants in the chemical bath may be diluted or the wet chemical process may be stopped completely.

In another illustrative embodiment, a target scatterometric trace may be created for the metal silicide regions 17 that corresponds to a minimum acceptable thickness for the metal silicide regions 17. Thereafter, after at least some portion of the wet chemical process is performed to remove the unreacted refractory metal 21, scatterometric measurements may be taken of the metal silicide regions 17. In one particular example, the wet chemical process may be stopped if the scatterometric measurements indicate that the thickness of the metal silicide region 17 is near or equal to the thickness associated with the target scatterometric trace. This may be determined by comparing the generated scatterometric trace with the target scatterometric trace using a variety of known techniques.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the controller 52, as described, is the Catalyst system offered by KLA Tencor, Inc. The Catalyst system uses Semiconductor Equipment and Materials International (SEMI) Computer Integrated Manufacturing (CIM) Framework compliant system technologies, and is based on the Advanced Process Control (APC) Framework. CIM (SEMI E81-0699—Provisional Specification for CIM Framework Domain Architecture) and APC (SEMI E93-0999—Provisional Specification for CIM Framework Advanced Process Control Component) specifications are publicly available from SEMI.

The present invention is generally directed to various methods of controlling wet chemical processes in forming metal silicide regions, and a system for performing same. In one illustrative embodiment, the method comprises providing a substrate having a layer of unreacted refractory metal and at least one metal silicide region formed thereabove, performing a wet chemical process to remove at least a portion of the layer of unreacted refractory metal, measuring at least one characteristic of the portion of the layer of unreacted refractory metal while the wet chemical process is being performed, and controlling at least one parameter of the wet chemical process based upon the measured at least one characteristic of the portion of the layer of unreacted refractory metal.

In another illustrative embodiment, the method comprises providing a substrate having a layer of unreacted refractory metal and at least one metal silicide region formed thereabove, performing a wet chemical process to remove at least a portion of the layer of unreacted refractory metal, measuring at least one characteristic of the portion of the layer of unreacted refractory metal after at least some of the wet chemical process has been performed, and controlling at least one parameter of the wet chemical process based upon the measured at least one characteristic of the portion of the layer of unreacted refractory metal.

In yet another illustrative embodiment, the method comprises providing a substrate having a layer of unreacted refractory metal and at least one metal silicide region formed thereabove, measuring at least one characteristic of at least a portion of the layer of unreacted refractory metal, determining at least one parameter of a wet chemical process to be performed to remove the layer of unreacted refractory metal based upon the measured characteristic, and performing the wet chemical process comprised of the determined parameter on the layer of unreacted refractory metal.

In a further illustrative embodiment, the method comprises providing a substrate having a layer of unreacted refractory metal and at least one metal silicide region formed thereabove, performing a wet chemical process to remove the layer of unreacted refractory metal, measuring at least a thickness of at least a portion of the layer of unreacted refractory metal after at least some of the wet chemical process has been performed, and controlling at least one parameter of the wet chemical process based upon the measured thickness of the portion of the layer of unreacted refractory metal.

In still a further illustrative embodiment, the method comprises providing a substrate having a layer of unreacted refractory metal and at least one metal silicide region formed thereabove, performing a wet chemical process to remove at least a portion of the layer of unreacted refractory metal, measuring a thickness of the metal silicide region at some point after the wet chemical process has been performed, and controlling at least one parameter of the wet chemical process based upon the measured thickness of the metal silicide region.

In yet a further illustrative embodiment, the method comprises providing a substrate having a layer of unreacted refractory metal and at least one metal silicide region formed thereabove, performing a wet chemical process to remove at least a portion of the layer of unreacted refractory metal, measuring a thickness of the metal silicide region at some point after the wet chemical process has been performed, and performing the wet chemical process for a fixed duration after the measured thickness has reached a preselected value.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method, comprising:
providing a substrate having a layer of unreacted refractory metal and at least one metal silicide region formed thereabove;
performing a wet chemical process to remove at least a portion of said layer of unreacted refractory metal;
measuring, using a scatterometry tool, at least one characteristic of said portion of said layer of unreacted refractory metal after at least a portion of said wet chemical process has been performed; and
controlling at least one parameter of said wet chemical process based upon said measured at least one characteristic of said portion of said layer of unreacted refractory metal.

2. The method of claim 1, wherein said at least one metal silicide region is formed on a feature comprised of at least one of a gate electrode, a source region, a drain region, a silicon-containing line, a resistor, a capacitor, a memory cell and a transistor.

3. The method of claim 1, wherein said refractory metal is comprised of at least one of cobalt, titanium, tantalum, nickel, platinum and tungsten.

4. The method of claim 1, wherein said at least one metal silicide region is comprised of at least one of cobalt silicide, titanium silicide, tantalum suicide, nickel silicide, platinum silicide and tungsten silicide.

5. The method of claim 1, wherein said at least one characteristic of said unreacted portions of said layer of refractory metal is at least one of a thickness, a surface profile, and a chemical stoichiometry of said portion of said layer of unreacted refractory metal.

6. The method of claim 1, wherein said at least one parameter of said wet chemical process is comprised of at least one of a temperature, a liquid flow rate, an etchant concentration and a duration of said wet chemical process.

7. The method of claim 1, further comprising modifying, based upon said measured characteristic of said unreacted portions of said layer of refractory metal, at least one parameter of at least one wet chemical process to be performed on at least one subsequently processed substrate to remove unreacted portions of a layer of refractory metal formed above said subsequently process substrate.

8. A method, comprising:
providing a substrate having a layer of unreacted refractory metal and at least one metal silicide region formed thereabove;
measuring, using a scatterometry tool, at least one characteristic of at least a portion of said layer of unreacted refractory metal;
determining at least one parameter of a wet chemical process to be performed to remove said layer of unreacted refractory metal based upon said measured characteristic; and
performing said wet chemical process comprised of said determined parameter on said layer of unreacted refractory metal.

9. The method of claim 8, wherein said at least one metal silicide region is formed on a feature comprised of at least one of a gate electrode, a source region, a drain region, a silicon-containing line, a resistor, a capacitor, a memory cell and a transistor.

10. The method of claim 8, wherein said refractory metal is comprised of at least one of cobalt, titanium, tantalum, nickel, platinum and tungsten.

11. The method of claim 8, wherein said at least one metal silicide region is comprised of at least one of cobalt silicide, titanium silicide, tantalum silicide, nickel silicide, platinum silicide and tungsten silicide.

12. The method of claim 8, wherein said wet chemical process is performed in a chemical bath tool.

13. The method of claim 8, wherein said at least one characteristic of said layer of unreacted refractory metal is at least one of a thickness, a surface profile, and a chemical stoichiometry of said portion of said layer of unreacted refractory metal.

14. The method of claim 8, wherein said determined at least one parameter of said wet chemical process is comprised of at least one of a temperature, a liquid flow rate, an etchant concentration and a duration of said wet chemical process.

15. A method, comprising:
providing a substrate having a layer of unreacted refractory metal and at least one metal silicide region formed thereabove;
performing a wet chemical process to remove said layer of unreacted refractory metal;
measuring at least a thickness of at least a portion of said layer of unreacted refractory metal after at least some of said wet chemical process has been performed; and
controlling at least one parameter of said wet chemical process based upon said measured thickness of said at least one portion of said layer of unreacted refractory metal.

16. The method of claim 15, wherein said step of measuring said at least one characteristic of at least a portion of said layer of unreacted refractory metal is performed using a scatterometry tool.

17. The method of claim 15, wherein said at least one metal silicide region is formed on a feature comprised of at least one of a gate electrode, a source region, a drain region, a silicon-containing line, a resistor, a capacitor, a memory cell and a transistor.

18. The method of claim 15, wherein said refractory metal is comprised of at least one of cobalt, titanium, tantalum, nickel, platinum and tungsten.

19. The method of claim 15, wherein said at least one metal silicide region is comprised of at least one of cobalt silicide, titanium silicide, tantalum silicide, nickel silicide, platinum silicide and tungsten silicide.

20. The method of claim 15, wherein said wet chemical process is performed in a chemical bath tool.

21. The method of claim 15, wherein said at least one parameter of said wet chemical process is comprised of at least one of a temperature, a liquid flow rate, an etchant concentration and a duration of said wet chemical process.

22. The method of claim 15, further comprising modifying, based upon said measured thickness of said at least one portion of said layer of unreacted refractory metal, at least one parameter of at least one wet chemical process to be performed on at least one subsequently processed substrate to remove at least a portion of a layer of unreacted refractory metal formed above said subsequently process substrate.

23. A method, comprising:
providing a substrate having a layer of unreacted refractory metal and at least one metal silicide region formed thereabove;
performing a wet chemical process to remove at least a portion of said layer of unreacted refractory metal; and
stopping said wet chemical process based upon a measured thickness of said layer of unreacted refractory metal.

24. The method of claim 23, wherein said measured thickness of said layer of unreacted refractory metal is obtained by a scatterometry tool.

25. The method of claim 23, wherein said measured thickness of said layer of unreacted refractory metal is obtained based upon a measurement taken as said wet chemical process is being performed.

26. A method, comprising:
providing a substrate having a layer of unreacted refractory metal and at least one metal silicide region formed thereabove;
performing a wet chemical process to remove at least a portion of said layer of unreacted refractory metal; and
stopping said wet chemical process based upon a measured thickness of said metal silicide region.

27. The method of claim 26, wherein said measured thickness of said metal silicide region is obtained by a scatterometry tool.

28. The method of claim 26, wherein said measured thickness of said metal silicide region is obtained based upon a measurement taken while said wet chemical process is being performed.

29. A method, comprising:
providing a substrate having a layer of unreacted refractory metal and at least one metal silicide region formed thereabove;
performing a wet chemical process to remove at least a portion of said layer of unreacted refractory metal;
measuring a thickness of said portion of said layer of unreacted refractory metal after at least a portion of said wet chemical process has been performed; and
controlling at least one parameter of said wet chemical process based upon said measured thickness of said portion of said layer of unreacted refractory metal.

30. The method of claim 29, wherein said step of measuring said thickness of said portion of said layer of unreacted refractory metal is performed using a scatterometry tool.

31. The method of claim 29, wherein said at least one parameter of said wet chemical process is comprised of at least one of a temperature, a liquid flow rate, an etchant concentration and a duration of said wet chemical process.

32. The method of claim 29, further comprising modifying, based upon said measured thickness of said unreacted portions of said layer of refractory metal, at least one parameter of at least one wet chemical process to be performed on at least one subsequently processed substrate to remove unreacted portions of a layer of refractory metal formed above said subsequently process substrate.

33. A method, comprising:
providing a substrate having a layer of unreacted refractory metal and at least one metal silicide region formed thereabove;
performing a wet chemical process to remove at least a portion of said layer of unreacted refractory metal;
measuring a surface profile of said portion of said layer of unreacted refractory metal after at least a portion of said wet chemical process has been performed; and
controlling at least one parameter of said wet chemical process based upon said measured surface profile of said portion of said layer of unreacted refractory metal.

34. The method of claim 33, wherein said step of measuring said surface profile of said portion of said layer of unreacted refractory metal is performed using a scatterometry tool.

35. The method of claim 33, wherein said at least one parameter of said wet chemical process is comprised of at least one of a temperature, a liquid flow rate, an etchant concentration and a duration of said wet chemical process.

36. The method of claim 33, further comprising modifying, based upon said measured surface profile of said unreacted portions of said layer of refractory metal, at least one parameter of at least one wet chemical process to be performed on at least one subsequently processed substrate to remove unreacted portions of a layer of refractory metal formed above said subsequently process substrate.

37. A method, comprising:
providing a substrate having a layer of unreacted refractory metal and at least one metal silicide region formed thereabove;
performing a wet chemical process to remove at least a portion of said layer of unreacted refractory metal;
measuring a chemical stoichiometry of said portion of said layer of unreacted refractory metal after at least a portion of said wet chemical process has been performed; and
controlling at least one parameter of said wet chemical process based upon said measured chemical stoichiometry of said portion of said layer of unreacted refractory metal.

38. The method of claim 37, wherein said at least one parameter of said wet chemical process is comprised of at least one of a temperature, a liquid flow rate, an etchant concentration and a duration of said wet chemical process.

39. The method of claim 1, further comprising modifying, based upon said measured chemical stoichiometry of said unreacted portions of said layer of refractory metal, at least one parameter of at least one wet chemical process to be performed on at least one subsequently processed substrate to remove unreacted portions of a layer of refractory metal formed above said subsequently process substrate.

40. A method, comprising:
providing a substrate having a layer of unreacted refractory metal and at least one metal silicide region formed thereabove;
measuring a thickness of at least a portion of said layer of unreacted refractory metal;
determining at least one parameter of a wet chemical process to be performed to remove said layer of unreacted refractory metal based upon said measured thickness; and
performing said wet chemical process comprised of said determined parameter on said layer of unreacted refractory metal.

41. The method of claim 40, wherein said step of measuring said thickness of said layer of unreacted refractory metal is performed using a scatterometry tool.

42. The method of claim 40, wherein said determined at least one parameter of said wet chemical process is comprised of at least one of a temperature, a liquid flow rate, an etchant concentration and a duration of said wet chemical process.

43. A method, comprising:
providing a substrate having a layer of unreacted refractory metal and at least one metal silicide region formed thereabove;
measuring a surface profile of at least a portion of said layer of unreacted refractory metal;
determining at least one parameter of a wet chemical process to be performed to remove said layer of unreacted refractory metal based upon said measured surface profile; and performing said wet chemical process comprised of said determined parameter on said layer of unreacted refractory metal.

44. The method of claim 43, wherein said step of measuring said surface profile of said layer of unreacted refractory metal is performed using a scatterometry tool.

45. The method of claim 43, wherein said determined at least one parameter of said wet chemical process is comprised of at least one of a temperature, a liquid flow rate, an etchant concentration and a duration of said wet chemical process.

46. A method, comprising:

providing a substrate having a layer of unreacted refractory metal and at least one metal silicide region formed thereabove;

measuring a chemical stoichiometry of at least a portion of said layer of unreacted refractory metal;

determining at least one parameter of a wet chemical process to be performed to remove said layer of unreacted refractory metal based upon said measured chemical stoichiometry; and performing said wet chemical process comprised of said determined parameter on said layer of unreacted refractory metal.

47. The method of claim 46, wherein said determined at least one parameter of said wet chemical process comprised of at least one of a temperature, a liquid flow rate, an etchant concentration of said wet chemical process.

* * * * *

UNITED STATES PATENT AND TRADEMARK OFFICE
CERTIFICATE OF CORRECTION

PATENT NO. : 6,790,683 B1
DATED : September 14, 2004
INVENTOR(S) : Richard J. Markle and Terri A. Couteau

It is certified that error appears in the above-identified patent and that said Letters Patent is hereby corrected as shown below:

Column 13,
Line 36, "suicide" should be -- silicide --.

Column 18,
Line 12, after "process" insert -- is --.
Line 14, after "concentration" insert -- and a duration --.

Signed and Sealed this

Fourteenth Day of December, 2004

JON W. DUDAS
*Director of the United States Patent and Trademark Office*